United States Patent
Kassman

[11] Patent Number: 5,885,205
[45] Date of Patent: Mar. 23, 1999

[54] CONDOM EXERTING LATERAL PRESSURE ON THE PENIS

[76] Inventor: Leon B. Kassman, 245 E. 24th St., New York, N.Y. 10010

[21] Appl. No.: 725,562

[22] Filed: Oct. 3, 1996

[51] Int. Cl.[6] .................................................. A61F 5/00
[52] U.S. Cl. ............................................. 600/38; 128/842
[58] Field of Search .................................. 128/842, 844, 128/918, 885; 604/347–353; 600/38–40

[56] References Cited

U.S. PATENT DOCUMENTS

| | | | |
|---|---|---|---|
| 1,225,341 | 5/1917 | Lederer | 600/38 |
| 3,809,090 | 5/1974 | Povlacs et al. | |
| 4,281,648 | 8/1981 | Rogers . | |
| 4,378,008 | 3/1983 | Osbon | 600/38 |
| 4,432,357 | 2/1984 | Pomeranz . | |
| 4,523,584 | 6/1985 | Yachia | 600/38 |
| 4,671,262 | 6/1987 | West | 600/39 |
| 4,829,991 | 5/1989 | Boeck | 600/38 |
| 4,852,586 | 8/1989 | Haines . | |
| 4,919,149 | 4/1990 | Stang . | |
| 5,377,692 | 1/1995 | Pfeil | 128/844 |
| 5,469,863 | 11/1995 | Shah | 128/844 |
| 5,513,652 | 5/1996 | Schwartz . | |
| 5,522,787 | 6/1996 | Evans . | |
| 5,549,924 | 8/1996 | Shlenker | 128/844 |
| 5,666,971 | 9/1997 | Anatolievich . | |
| 5,715,839 | 2/1998 | Strauss et al. . | |

OTHER PUBLICATIONS

Hoag Levins, *American Sex Machines*, pp. 89–93, 102–110, 1996, Holbrook, Massachusetts.

*Primary Examiner*—Michael A. Brown
*Attorney, Agent, or Firm*—Abelman, Frayne & Schwab

[57] ABSTRACT

A condom that exerts lateral pressure on the penis of a user is disclosed. The lateral pressure is exerted by the geometry of the condom itself upon application or is exerted by means for exerting such lateral pressure located on the condom which means are activated by the user after the condom is applied. User activated lateral pressure is controllable by the user within safe limits. The lateral pressure prevents loss of erection after application of the condom and increases the size, hardness, and duration of the user's erection.

24 Claims, 6 Drawing Sheets

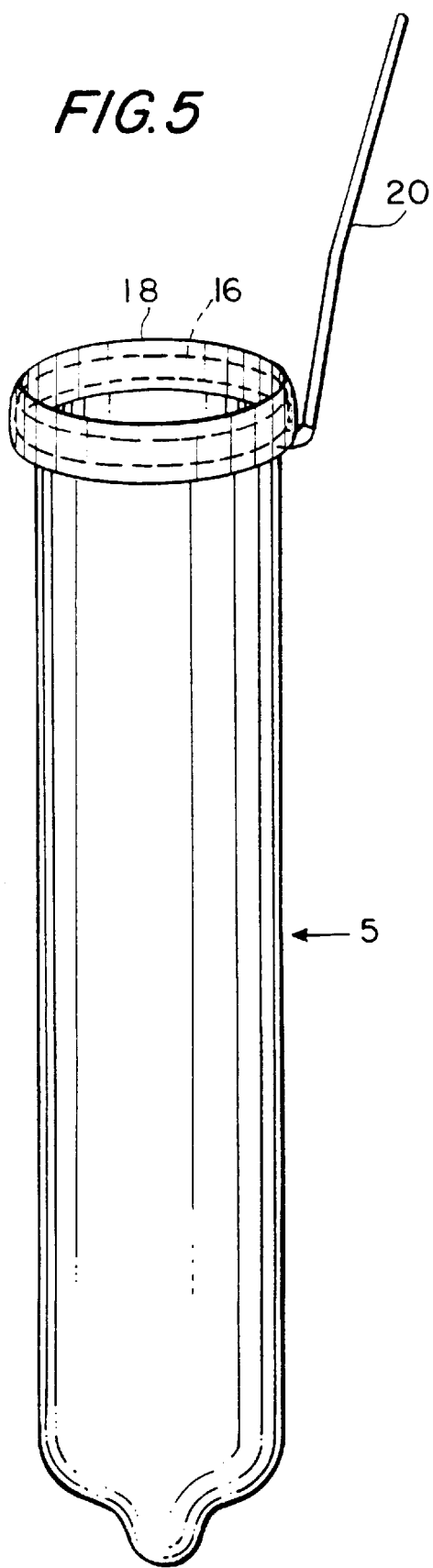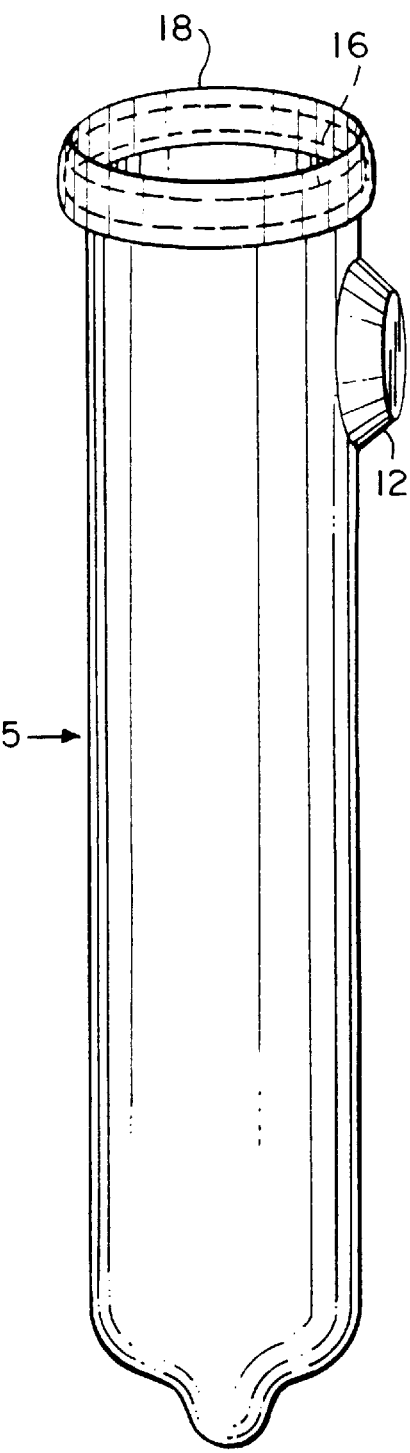

CONDOM EXERTING LATERAL PRESSURE ON THE PENIS

BACKGROUND OF THE INVENTION

1. Field of the Invention

This invention relates to condoms for use by male persons during sexual intercourse and, more particularly, to condoms that are of variable stiffness.

2. Description of the Related Art

The earliest published description of the condom was by the Italian anatomist Gabriel Fallopius in 1564. Early condoms were generally made from animal intestines or fish membrane and were mostly used to prevent the sexual transmission of disease, a task which they often inefficiently performed. However, by the 17th century, condoms were used as a contraceptive as well.

Most condoms were made of vulcanized rubber from the 1840s to the 1930s after the discovery of the process for vulcanization of rubber by Charles Goodyear in 1839, and condoms have been a popular, efficient, and generally convenient contraceptive method since the second half of the 19th century. Since the 1930s most condoms have been made from latex. (The above historical material is based on information from *The New Encyclopedia Britannica*, Vol. 3, p. 522, Vol. 15, p. 114, 15th Edition, Encyclopedia Britannica, Inc., 1990.)

Recently with the large increase in births out of wedlock in the United States of America and many other western countries and the outbreak of Auto-Immune Deficiency Syndrome (AIDS) globally, the use of condoms as a contraceptive method and as a method of preventing the spread of sexually transmitted diseases has become urgent, both from a medical point of view and a societal point of view.

However, there are certain well known drawbacks to the use of condoms, at least from the point of view of the male user. Some of these drawbacks are the inconvenience and delay occasioned by the necessity of applying a condom immediately prior to intercourse when an erection of the penis is present. The often cumbersome process of applying the condom can result in a loss of erection during the time required for application making the condom useless and resulting in the frustration of the user. Even if application is successful, many male users complain of a loss of sensation and pleasure due to the interposition of the condom between the penis and the vagina during intercourse. These drawbacks cause condoms to be irregularly used and, thus, to fail to fulfill their purposes.

U.S. Pat. No. 4,281,648 issued to Rogers discloses an inflatable condom with a conventional tubular anterior portion apparently fitting over the base and lower shaft of the penis and an inflatable secondary portion extending from the anterior portion inflated by an air duct extending from the anterior portion to the secondary portion. Rogers purportedly enlarges the size of the penis in order to compensate for maladjustment in the two partners during coition.

However, Rogers seems to produce this enlargement only through the enlargement achieved by the inflatable secondary portion. In particular, there is minimal or no enlargement of the penis itself through lateral pressure since minimum ballooning of inner wall 12, presumably in contact with the penis after application of the condom, is desired when the expandible sheath 5 included in the secondary portion is inflated, (column 3, lines 37–41). Thus, it seems that Rogers increases the apparent size of the user's penis as sensed by the female participant without materially increasing the actual size of the user's penis or improving the user's erection. Moreover, the location of application of whatever pressure is exerted on the user's penis in Rogers seems to be at the end of the shaft of the user's penis and at the glans. Rogers fails to disclose or suggest pressure at the base of the penis, the most advantageous place to apply pressure in order to improve a user's erection and increase the size of the user's erect penis, as will be explained below.

This invention overcomes the drawbacks of Rogers by increasing the size of the user's erect penis, and increasing the duration and hardness of the user's erection through exertion of lateral pressure in locations designed to produce these results, especially including the base of the user's penis.

U.S. Pat. No. 4,432,357 issued to Pomeranz discloses a condom which has a deformable chamber or chambers filled with a rheopexic fluid. A rheopexic fluid has the characteristic of thickening with increasing shear stress. The movements during intercourse allegedly create such shear stress causing the thickening of the fluid and the stiffening of the condom. This stiffening of the condom simulates an erection, (column 3, lines 32–36). This stiffening also creates pressure around the base end of the penis at least in one embodiment, thereby prolonging a user's erection by prolonging the time required for disengorgement of blood vessels within the penis, according to the disclosure in Pomeranz, (column 5, lines 1–8).

Pomeranz, although purportedly addressing the problem of a loss of pleasure, does not ameliorate the problem of a loss of erection during application since any stiffening effect would normally only occur during intercourse. Moreover, Pomeranz relies on the use of a rather exotic material, namely, the rheopexic fluid to achieve the desired stiffening effect.

This invention eliminates the drawbacks of Pomeranz by preventing a loss of erection during and after application of the condom and achieves its improvement of the user's erection with the use of readily available methods and without resorting to the use of exotic substances.

This invention makes substantial progress in overcoming the problem of a loss of sensation and pleasure during intercourse, thereby encouraging the more widespread use of condoms, particularly as a contraceptive method and as a measure to prevent the spread of sexually transmitted diseases.

SUMMARY OF THE INVENTION

The invention comprises a condom with an added means for exerting lateral pressure on the shaft of the penis. The lateral pressure exerted will preferably be exerted around the circumference of the penis although pressure can be exerted along the length of the penis in addition to or in place of circumferential pressure. The pressure exerting means will typically be activated by the user at the time of application, by the injection of air into the pressure means or by alternative mechanical means, thereby assuring the continuation of his erection. Moreover, the pressure exerting means will tend to increase the duration of the erection and the hardness and size of the user's erect penis, thereby compensating for any loss of pleasure due to the wearing of the condom during intercourse.

An object of this invention is to supply a condom which prevents the loss of erection during application of the condom.

A further object of the invention is to supply a condom which exerts lateral pressure on the penis of a wearer.

A further object of the invention is to supply a condom which exerts such lateral pressure by readily available means.

A still further object of the invention is to supply a condom which exerts such lateral pressure at locations designed to increase the size and hardness of the user's penis during erection and the duration of the erection.

A still further object of the invention is to supply a condom which compensates for any loss of pleasure during sexual intercourse with the condom applied by increasing the size and hardness of the user's penis during erection, increasing the duration of the user's erection, and increasing the frictional forces on the user's penis during intercourse.

A yet further object of the invention is to achieve all of the previously mentioned objects without causing injury to the user and consistent with the comfort of the user.

These and other objects and advantages of the present invention will become more apparent to those of ordinary skill in the art upon consideration of the attached drawings and the following description of the preferred embodiments which are meant by way of illustration and example only, but are not to be construed as in any way limiting the invention disclosed and claimed herein.

BRIEF DESCRIPTION OF THE DRAWINGS

FIG. 1a is a sectional view of FIG. 1 taken along section lines 1a—1a in FIG. 1.

FIG. 4 is a perspective view of a fourth embodiment of the invention.

FIG. 5 is a perspective view of a fifth embodiment of the invention.

DESCRIPTION OF THE PREFERRED EMBODIMENTS

For a more detailed description of the invention in its several embodiments, given only by way of example and not to be construed as limiting the invention in any fashion, we refer to the drawings.

Figure 1:
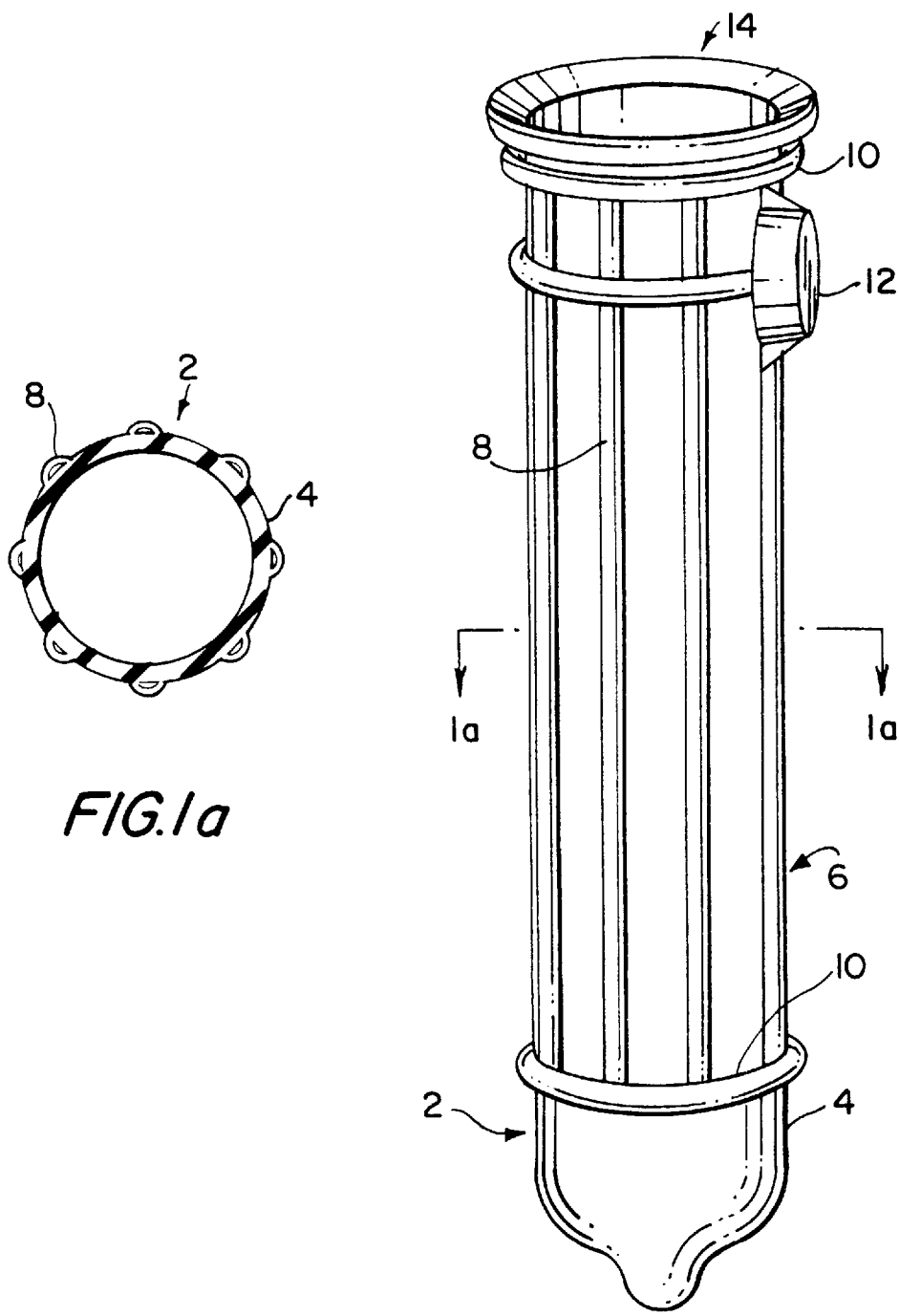
FIG. 1 is a perspective view of a first embodiment of the invention.

FIG. 1 represents the first embodiment of the invention. In this embodiment, a condom 2 comprises a membrane 4, contacting the penis of the user, on which membrane is formed or applied microtubules 6. The membrane 4 has a circular cross-section (see FIG. 1a) and is cylindrical in shape when extended, the same as other conventional condoms. Such microtubules 6 comprise longitudinal microtubules 8, which extend along a portion of the length of the condom 2 and circumferential microtubules 10 which extend around the circumference of the condom 2. The condom 2 also comprises an inflation compartment 12. The condom 2 is preferably made from polyurethane or other equivalent material allowing the formation of the microtubules 6 when the condom 2 is heat treated or dipped, depending upon the process of manufacture utilized. The heat treatment or dipping causes the fibers of the polyurethane or other equivalent material to align and form the microtubules 6. Polyurethane also has the advantage of being less permeable to viruses than latex, for example, a conventional condom material.

FIG. 1 shows the condom 2 after inflation. Such inflation will be accomplished through the use of air injected through the inflation compartment 12. Such air can be injected through the crushing of a compressed air pellet (not shown) placed in the inflation compartment 12, through an external tube (not shown) leading into the inflation compartment 12 from an air pump (not shown), or through an external tube (not shown) supplied with air by aspiration of the user or another person. The air injected into the inflation compartment 12 will pass from there through the microtubules 6 which, for example, have internal apertures connecting all the microtubules 6 and the inflation compartment 12 together. Alternatively, the microtubules 6 may be connected to the inflation compartment 12 by any method known to one with ordinary skill in the art. A one-way valve or valves, seal or seals, or other equivalent device(s) (not shown) are placed in appropriate location(s) in the microtubules 6, inflation compartment 12, or in both to insure that the microtubules 6 retain any air injected into them.

The air in the microtubules 6 will exert lateral pressure on the user's penis around the circumference of the penis due to the circumferential microtubules 10 and along the length of the user's penis due to the longitudinal microtubules 8. This lateral pressure on the user's penis acts in a manner akin to a tourniquet placed on another part of the user's body. A tourniquet traps blood in those portions of the body to one side of the tourniquet which are further distant from the center of mass of the body and, thus, is effective in stopping bleeding. In the same way, the lateral pressure exerted on the user's penis by the microtubules 6 will trap blood in the user's penis. Since an erection is ordinarily caused by an increase in the supply of arterial blood to blood interspaces in the three cylindrical masses of cavernous tissue of which the penis is comprised, see *Anatomy of the Human Body*, pp. 1310, 1314, by Henry Gray, Charles Mayo Goss, editor, 29th American Edition, Lea & Febiger, 1973, the trapping of such blood will increase the size, hardness, and duration of a user's erection, thereby increasing the stimulation and pleasure of the user.

In particular, it is highly preferable that at least one of the circumferential microtubules 10 be located at the open base 14 of the condom 2 located at the base of the user's penis when the condom is applied thereto. Such a location of at least one of the circumferential microtubules 10 will apply circumferential pressure to the base of the user's penis acting in a way most analogous to the tourniquet previously mentioned and trapping as much blood as possible in the user's penis.

The longitudinal microtubules 8 primarily will aid the user in maintaining his erection through the stiffening effect achieved by the pressure which they exert laterally to the user's penis and longitudinally along the length of the user's penis. Such longitudinal microtubules 8 will additionally act to further secure the condom onto the erect penis of the user as well as onto the partially flaccid penis of the user after ejaculation. This characteristic will help solve the problem of the condom slipping off the penis after ejaculation and before or during withdrawal of the penis from the vagina.

The microtubules 6 will also increase stimulation during sexual intercourse because the microtubules 6 increase the surface area of the condom 2 over that of a conventional condom, thereby increasing the potential contact area between the condom 2 and the vaginal walls over the contact area obtained with or without a conventional condom. This increased contact area and the increased frictional forces generated will provide increased stimulation and pleasure for the male and female participant. Moreover, the circumferential microtubules 10 will exert circumferential pressure on the shaft of the penis, resulting in a bulging of the side of the shaft of the penis which is more distant from the center of mass of the body relative to the circumferential microtubules 10. Such bulging, when in close proximity to the vaginal wall during intercourse, will create increased frictional forces over those present in the absence of such bulging, resulting in increased stimulation and pleasure for the male and female participant.

It should be understood that the microtubules will be designed to accommodate an air pressure that is the maximum safe value for the user. The pressure should be such a maximum to achieve the maximum blood trapping and stiffening effect on the penis of the user, but cannot exceed the maximum, lest injury result to the user.

Thus, the walls of the microtubules 6 may be designed so that they rupture if the user attempts to introduce an air pressure beyond the maximum safe value into them. Alternatively, the microtubules 6 may be designed to balloon in such a way as to make the condom unusable if the user attempts to introduce an unsafe air pressure into them. It should be noted that any inflation must be completed before intercourse to prevent any injury to the female participant if a condom fails due to overinflation in one of the ways previously described. Of course, the user through the use of an air pump or selected air pellets may select any air pressure less than the maximum safe value in accordance with the comfort of the user.

The condom 2 will be applied initially as a conventional condom is applied, either manually or by means of any condom applicator or similar contrivance. At the time of the application, the user will be required to have an erection as is required for the application of a conventional condom. After application and before sexual intercourse, air will be injected into the condom 2 through the inflation compartment 12 until the air pressure in the microtubules 6 reaches the comfort level of the user or the maximum safe value, whichever is less.

Figure 2:
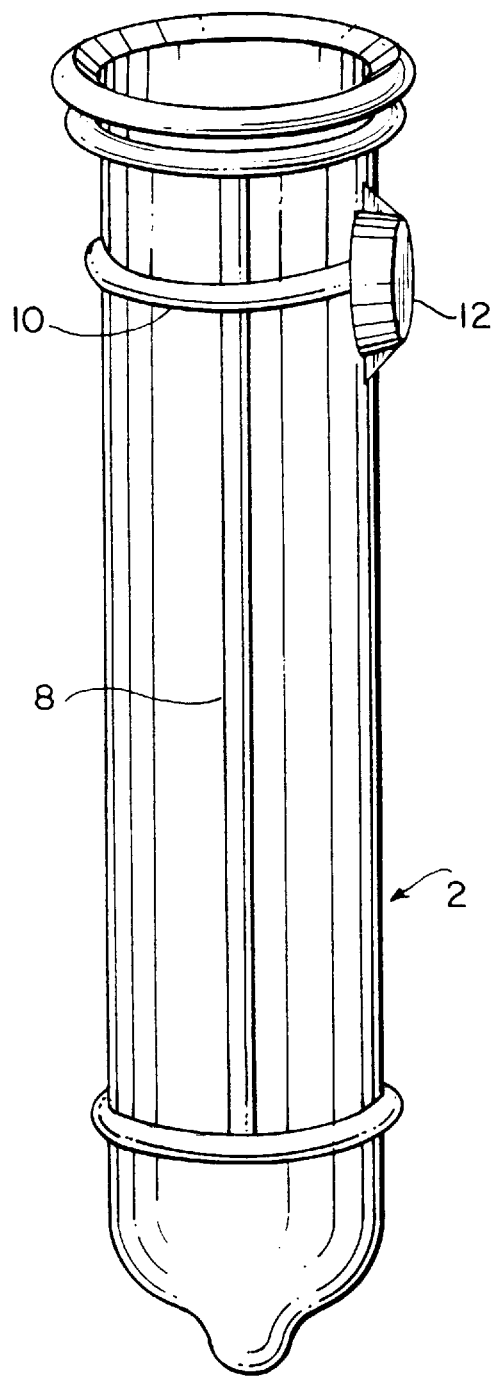
FIG. 2 is a perspective view of a second embodiment of the invention.

A second embodiment of the invention is shown in FIG. 2. The sole difference from the first embodiment is that, instead of a plurality of longitudinal microtubules 10 as shown in FIG. 1, only one longitudinal microtubule 8 is shown in FIG. 2. Such an arrangement of only one longitudinal microtubule 8 would be directed more toward stiffening the condom rather than exerting significant lateral and longitudinal pressure along the length of the user's penis.

Figure 3:
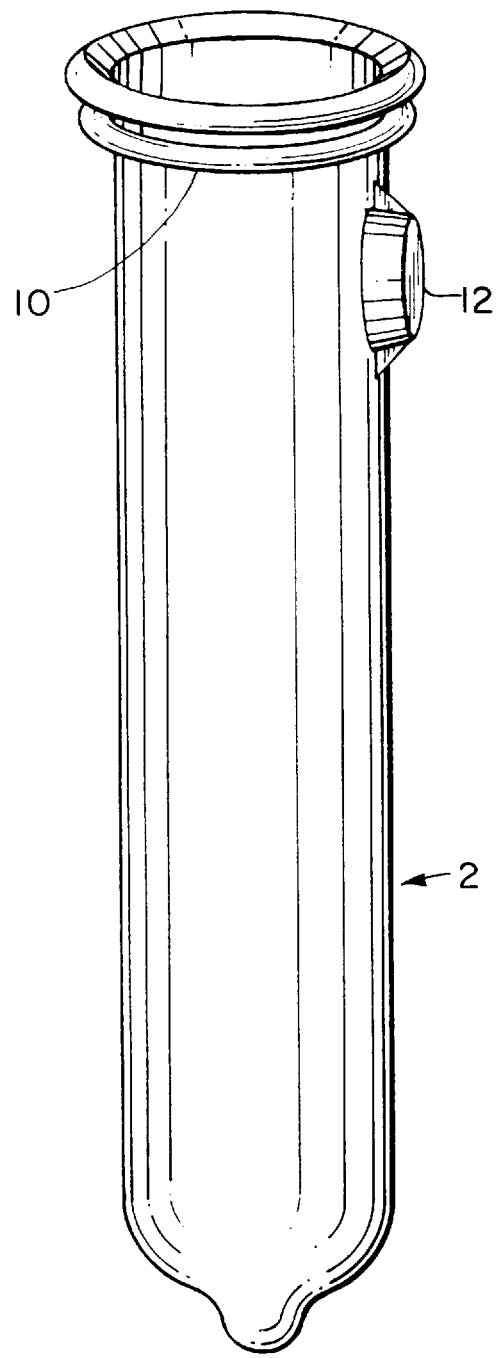
FIG. 3 is a perspective view of a third embodiment of the invention.

FIG. 3 shows a third embodiment of the invention. The third embodiment differs from the first two embodiments in that only one circumferential microtubule 10 is present and no longitudinal microtubules 8 are present in contrast to the first two embodiments in which at least one longitudinal microtubule 8 is present and a plurality of circumferential microtubules 10 are present. The one circumferential microtubule 10 present is placed at the base of the condom so as to attain maximum safe tourniquet effect for only one microtubule since that microtubule will apply a tourniquet force to the base of the penis. However, additional tourniquet, stiffening, and lateral forces provided by additional circumferential microtubules 10 and longitudinal microtubules 8 are absent.

FIG. 4 shows the fourth embodiment of the invention. In contrast to the first three embodiments of the invention, the condom 5 is made from a conventional condom material, latex, and it contains no microtubules 6. An inflation compartment 12 is also present as in the previous three embodiments with an analogous purpose to inject air into the condom 4 by any of the means previously disclosed. However, instead of injecting air into microtubules 6, the air is injected into a toroidal chamber 16 within a hollow lip 18 at the open end of the condom 5. Upon air being injected into the toroidal chamber 16, the chamber exerts circumferential and lateral pressure like a tourniquet on the base of the user's penis in a manner fully analagous to that of the circumferential microtubules 10 located at the base 14 of the condom 2 in the first three embodiments of the invention. Similarly to the first three embodiments of the invention, at least a single one-way valve, seal, or other equivalent means are located in appropriate location(s) in the inflation compartment 12, toroidal chamber 16, or in both to insure that the toroidal chamber 16 retains any air injected into it. This embodiment has the advantages of using a conventional condom material such as latex, instead of polyurethane, and the elimination of the difficulty involved in manufacturing a condom with microtubules, replacing them with a single toroidal chamber 16.

The fifth embodiment of the invention is shown in FIG. 5. It differs from the fourth embodiment of the invention in that a tube 20 leading directly to an air pump (not shown) or to the mouth of a user or other person is used to feed air directly into the toroidal chamber 16, instead of through an inflation compartment. This has the advantage of simplicity of construction since it eliminates the need for an inflation compartment 12, but this embodiment limits the mode of inflation to one which is based on a tube 20, whereas an inflation compartment, as in the fourth embodiment of the invention, can accommodate an air pellet as well.

Figure 6:
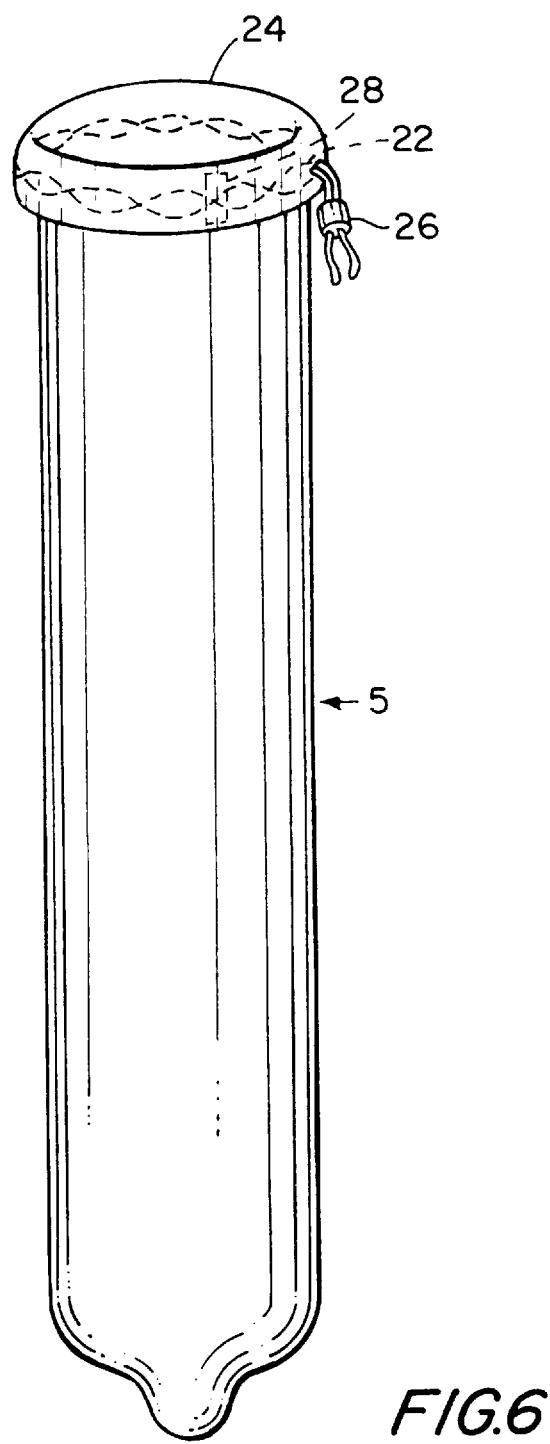
FIG. 6 is a perspective view of a sixth embodiment of the invention.

The sixth embodiment of the invention is shown in FIG. 6. Like the fourth and fifth embodiments, it too is constructed from latex. It differs in that no air or other gaseous means are provided to exert the lateral pressure needed. Instead a linear tightening device 22 is located in a hollow lip 24 at the open end of the condom 5. A bead or other adjustment device 26 is located on the linear tightening device 22 on the outside of the lip 24 to allow the user to tighten the linear tightening device 22 around the base of his penis after the application of the condom 5 to achieve the desired lateral pressure and tourniquet effect. The bead or other adjustment device 26 preferably comprises a locking mechanism (not shown), such as interlocking teeth, for example, and a means (not shown) for assuring instant manual release of the bead or adjustment device 26, such as by squeezing apart the locking mechanism, for example. The locking mechanism serves a function analagous to that of the one-way valve(s), seal(s), or equivalent device(s) in the first five embodiments of the invention, namely, assuring a constant lateral pressure on the user's penis. The instant manual release allows an added function, not present in the first five embodiments. It will allow the release of the lateral pressure entirely at any time. In contrast, the one-way pressure devices on the first five embodiments only allow for the maintenance or increase of lateral pressure, not the decrease of lateral pressure. Furthermore, the first five embodiments only contemplate the increase of lateral pressure prior to intercourse because of the danger to the female partner from condom failure due to overinflation during intercourse. This embodiment of the invention, however, allows increase of lateral pressure during intercourse with no danger to the female participant since no overinflation risk is present.

Some means, however, must be available to prevent the user from endangering himself by tightening the linear tightening device 22 excessively. Such means can, for example, take the form of a stop 28 located on the linear tightening device 22, preventing the reduction of the circumference of the linear tightening device 22 beyond a certain amount. The sixth embodiment of the invention has the advantage of simplicity of construction and use over the other embodiments since it relies on simple mechanical means to achieve the desired lateral pressure.

It should be understood that, although the word circumference has been used repeatedly in connection with the invention and the term normally refers to the perimeter of a circle, in this application the term should be interpreted broadly to also include the perimeter of any closed shape. In particular, in this connection, it should be noted that although conventional condoms are circular in cross-section and, therefore, cylindrical when extended, as were the first six embodiments of the invention disclosed herein, it may be preferable for the condoms disclosed and claimed herein to be substantially triangular in cross section to achieve the maximum lateral pressure on the penis of a user, given a certain air pressure or amount of other constricting force. This is because an erect penis "assumes the form of a triangular prism with rounded angles", see Anatomy of the Human Body, p. 1310, by Henry Gray, Charles Mayo Goss, editor, 29th American Edition, Lea & Febiger, 1973. Thus, a condom with a substantially triangular cross section, in particular, a cross section in the shape of a triangle with rounded corners, and assuming the shape of a triangular prism when extended achieves a tighter fit on the erect penis of a user than a conventionally shaped condom and exerts more lateral pressure on the penis for a given air pressure or amount of other constricting force.

Figures 7, 7A:
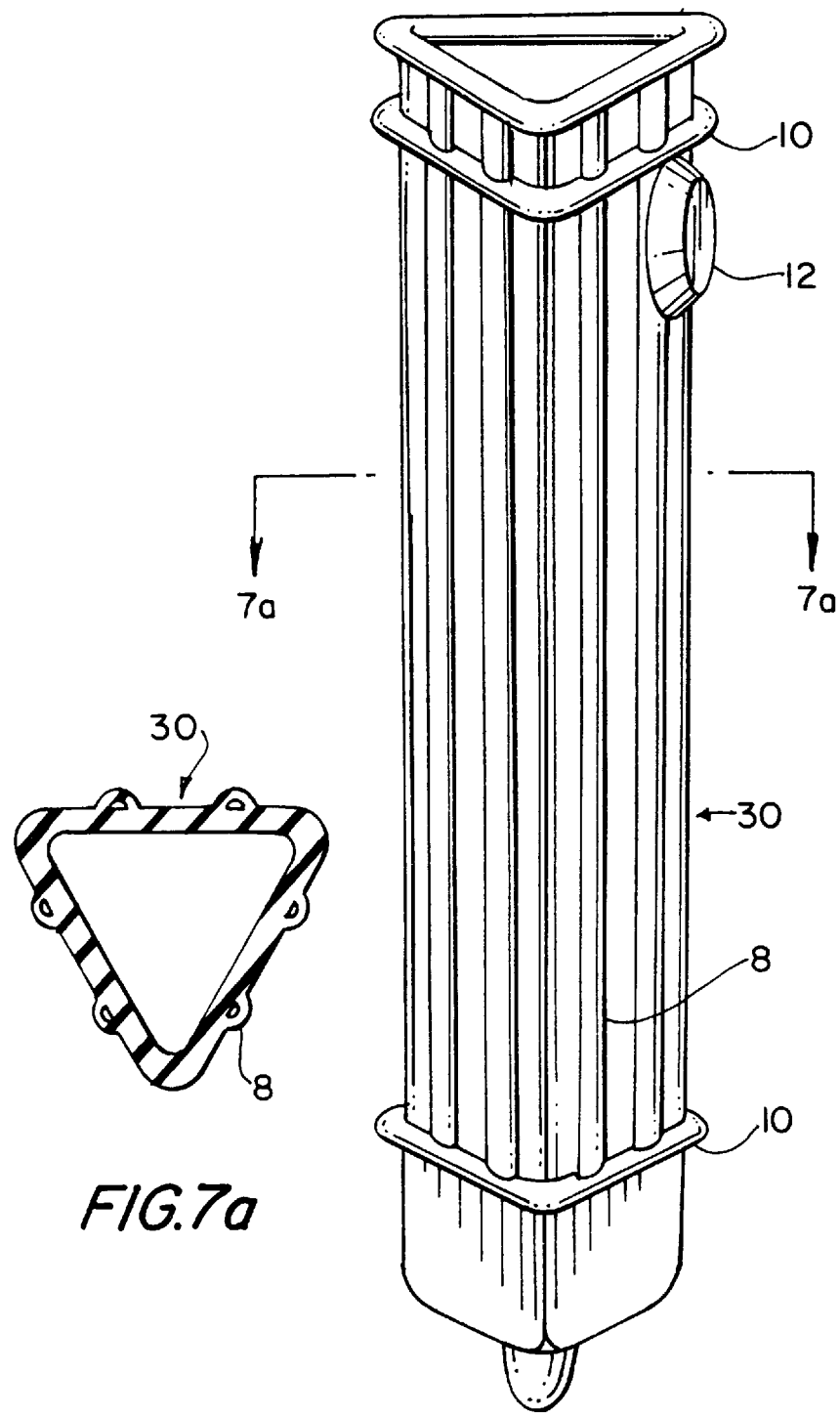
FIG. 7 is a perspective view of a seventh embodiment of the invention.
FIG. 7a is a sectional view of FIG. 7 taken along section lines 7a—7a in FIG. 7.

FIG. 7 shows the seventh embodiment of the invention which is such a condom 30 with a substantially triangular cross-section (see FIG. 7a). The condom 30 has circumferential microtubules 10, longitudinal microtubules 8, and an inflation compartment 12 just as the first embodiment of the invention does, and it is applied and inflated by methods completely the same as the first embodiment of the invention. Although a maximum lateral pressure on the penis of a user for a given air pressure or other amount of constricting force will be achieved by this embodiment, some users may prefer the looser fit of a conventional cylindrical condom and the consequent lower lateral pressure offered by the first six embodiments of the invention, based upon the personal comfort of the user.

Figures 8, 8A:
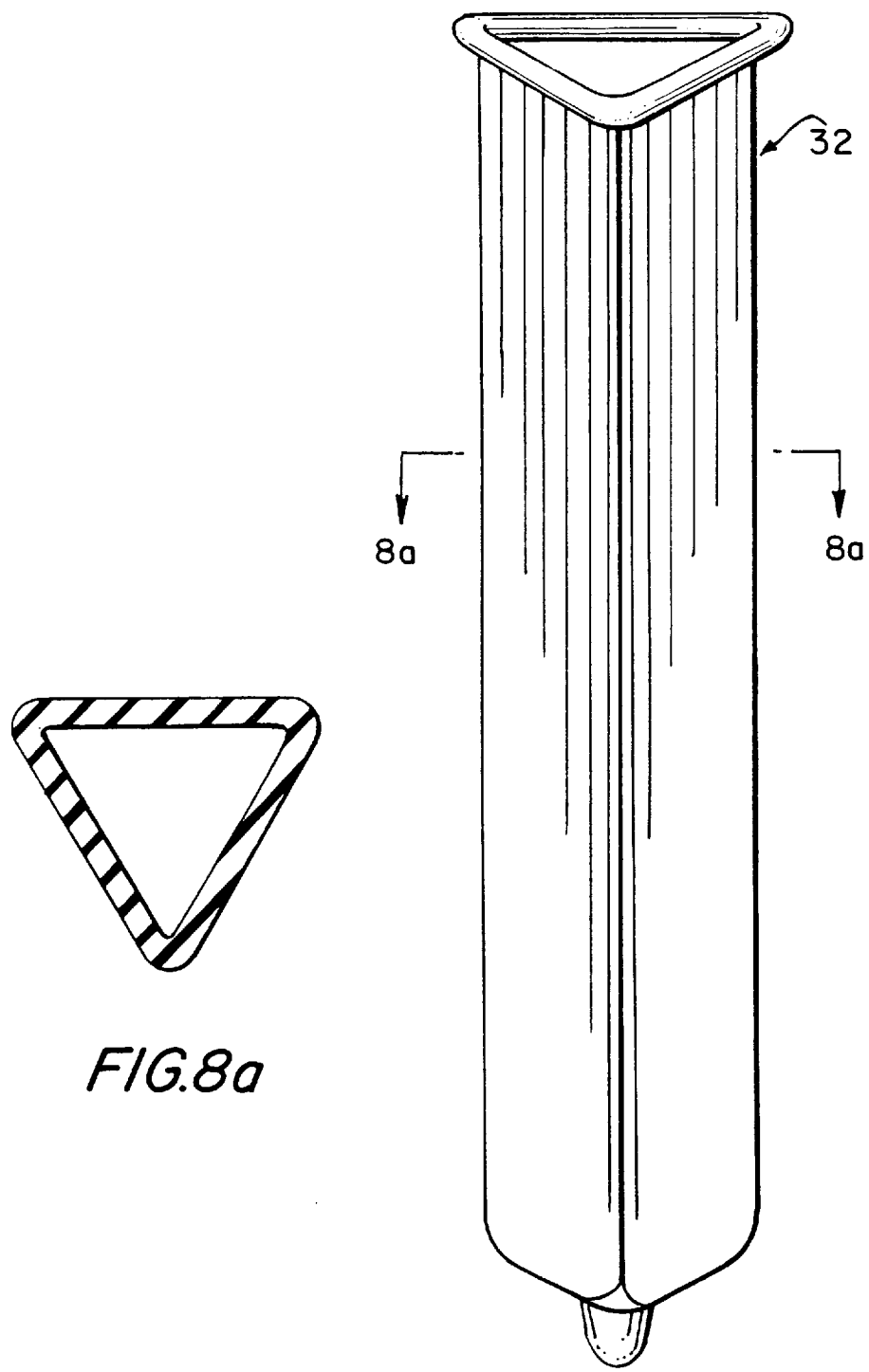
FIG. 8 is a perspective view of an eighth embodiment of the invention.
FIG. 8a is a sectional view of FIG. 8 taken along section lines 8a—8a in FIG. 8.

FIG. 8 shows the eighth embodiment of the invention which is a conventional condom except that the condom 32 shown has a substantially triangular cross-section (see FIG. 8a). This condom 32 exerts greater lateral pressure on the erect penis of a user than does a conventional condom, due to a tighter fit as previously explained.

While preferred embodiments have been described herein, it will be understood by those with ordinary skill in the art that various modifications, changes, or alterations may be made to the invention disclosed and described herein without departing from its scope or its equivalent as claimed in the appended claims. Thus, for example, as mentioned above, the condom disclosed and claimed herein may be of a circular cross-section, substantially triangular cross-section, or any other closed cross-sectional shape as appropriate to achieve maximum comfortable and safe lateral pressure on the penis of a user. In particular, although the first six embodiments of the invention were shown as having circular cross-sections, (see FIG. 1a), and, therefore, being cylindrical when extended, it would readily occur to one with ordinary skill in the art that their cross-sections could be made in a substantially triangular shape or any other closed shape appropriate to produce maximum safe and comfortable lateral pressure on the penis of a user.

Furthermore, some or all of the microtubules 6 or the toroidal chamber 16 may be prefilled with air or another pressure exerting gas or substance, instead of filling them with air upon application of the condom.

What is claimed is:

1. A means for tightly enclosing a user's penis to improve the user's erection when the user's penis is in an erect state, said means comprising:
   a. a tubular membrane open at a first end and closed at a second end, said tubular membrane adapted to be applied to the exterior of the skin of the user's penis; and
   b. means for exerting lateral compressive pressure on said user's penis, at least a portion of said means for exerting lateral compressive pressure being irremovably joined with said tubular membrane, said means for exerting lateral compressive pressure comprising a plurality of circumferential pressure exerting members disposed longitudinally and separately from one another along a length of said tubular membrane, said lateral compressive pressure being exerted in at least one region to improve the user's erection, said lateral compressive pressure being exerted without the application of shear stress to said tubular membrane.

2. A means for tightly enclosing a user's penis as claimed in claim 1, wherein said tubular membrane is made from polyurethane.

3. A means for tightly enclosing a user's penis as claimed in claim 1, wherein said tubular membrane is made from latex.

4. A means for tightly enclosing a user's penis as claimed in claim 1, wherein said tubular membrane has a circular cross-section, said cross-section being taken perpendicularly to a central axis of said tubular membrane.

5. A means for tightly enclosing a user's penis as claimed in claim 1, wherein said at least one region in which said lateral compressive pressure is being exerted comprises a perimeter of said user's penis, said perimeter being located at a base of said user's penis.

6. A means for tightly enclosing a user's penis as claimed in claim 1, wherein said means for exerting lateral compressive pressure on said user's penis comprises at least one microtubule.

7. A means for tightly enclosing a user's penis as claimed in claim 6, wherein said at least one microtubule comprises at least one circumferential microtubule.

8. A means for tightly enclosing a user's penis as claimed in claim 7, wherein said means for exerting lateral compressive pressure on said user's penis further comprises an inflation compartment.

9. A means for tightly enclosing a user's penis as claimed in claim 8, further comprising a means for maintaining a nondecreasing amount of said lateral compressive pressure on said user's penis.

10. A means for tightly enclosing a user's penis as claimed in claim 6, wherein said at least one microtubule comprises at least one longitudinal microtubule.

11. A means for tightly enclosing a user's penis as claimed in claim 10, wherein said means for exerting lateral compressive pressure on said user's penis further comprises an inflation compartment.

12. A means for tightly enclosing a user's penis as claimed in claim 11, further comprising a means for maintaining a nondecreasing amount of said lateral compressive pressure on said user's penis.

13. A means for tightly enclosing a user's penis as claimed in claim 1, wherein said means for exerting lateral compressive pressure on said user's penis comprises a hollow lip at said first end of said tubular membrane.

14. A method for applying a means for tightly enclosing a user's penis as claimed in claim 1 to said user's penis, comprising the steps of:
   a. applying said tubular membrane to said user's penis when said penis is in an erect state; and
   b. exerting lateral compressive pressure on said penis using said means for exerting lateral compressive pressure on said user's penis.

15. A method for applying a means for tightly enclosing a user's penis as claimed in claim 14, wherein said lateral compressive pressure is exerted by air.

16. A method for applying a means for tightly enclosing a user's penis as claimed in claim 14, wherein said lateral compressive pressure is exerted by means for tightening around said user's penis.

17. A means for tightly enclosing a user's penis to improve the user's erection when the user's penis is in an erect state, said means comprising:
   a. a tubular membrane open at a first end and closed at a second end, said tubular membrane adapted to be applied to the exterior of the skin of the user's penis; and
   b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the application of shear stress to said tubular membrane;
wherein said tubular membrane has a substantially triangular cross-section, said cross-section being taken perpendicularly to a central axis of said tubular membrane.

18. A means for tightly enclosing a user's penis to improve the user's erection when the user's penis is in an erect state, said means comprising:
   a. a tubular membrane open at a first end and closed at a second end, said tubular membrane adapted to be applied to the exterior of the skin of the user's penis; and
   b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the application of shear stress to said tubular membrane;
wherein said means for exerting lateral compressive pressure on said user's penis comprises a hollow lip at said first end of said tubular membrane, said hollow lip forming a toroidal chamber contained within said lip.

19. A means for tightly enclosing a user's penis to improve the user's erection when the user's penis is in an erect state, said means comprising:
   a. a tubular membrane open at a first end and closed at a second end, said tubular membrane adapted to be applied to the exterior of the skin of the user's penis; and
   b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the application of shear stress to said tubular membrane;
wherein said means for exerting lateral compressive pressure on said user's penis comprises a hollow lip at said first end of said tubular membrane, said means for exerting lateral compressive pressure on said user's penis further comprising means for tightening around said user's penis, said means for tightening being contained within said hollow lip.

20. A means for tightly enclosing a user's penis as claimed in claim 19, wherein said means for tightening around said user's penis comprises a cord and means for tightening said cord.

21. A means for tightly enclosing a user's penis as claimed in claim 20, wherein said means for tightening said cord comprises a means for locking said means for tightening said cord in a certain position on said cord and a means for manually releasing said means for tightening said cord when said means for tightening said cord is in a locked position.

22. A method for applying a means for tightly enclosing a user's penis to improve the user's erection when the user's penis is in an erect state, said means comprising:
   a. a tubular membrane open at a first end and closed at a second end, said tubular membrane adapted to be applied to the exterior of the skin of the user's penis; and
   b. means for exerting lateral compressive pressure on said user's penis, at least a portion of said means for exerting lateral compressive pressure being irremovably joined with said tubular membrane, said lateral compressive pressure being exerted in at least one region to improve the user's erection, said lateral compressive pressure being exerted without the application of shear stress to said tubular membrane;
said method comprising the steps of:
   a. applying said tubular membrane to said user's penis when said penis is in an erect state; and
   b. exerting lateral compressive pressure on said penis using said means for exerting lateral compressive pressure on said user's penis;
wherein said lateral pressure is exerted by means for tightening around said user's penis, said means for tightening around said user's penis comprising a cord and means for tightening said cord.

23. A means for tightly enclosing a user's penis to improve the user's erection when the user's penis is in an erect state, said means comprising a tubular membrane open at a first end and closed at a second end, said tubular membrane being applied to the exterior of the skin of the user's penis, said tubular membrane exerting lateral compressive pressure on the user's penis, said tubular membrane having a substantially triangular cross-section, said cross-section being taken perpendicularly to a central axis of said tubular membrane.

24. A method for applying a means for tightly enclosing a user's penis as claimed in claim 23 to said user's penis comprising the step of applying said tubular membrane to said user's penis when said penis is in an erect state.

* * * * *